United States Patent
Rubio Guivernau et al.

(10) Patent No.: US 9,310,563 B2
(45) Date of Patent: Apr. 12, 2016

(54) INTEGRATED SYSTEM FOR ACTIVE EQUALIZATION OF CHROMATIC DISPERSION

(75) Inventors: José Luis Rubio Guivernau, Madrid (ES); Eduardo Margallo Balbás, Madrid (ES)

(73) Assignee: Medlumics S.L., Madrid (ES)

( * ) Notice: Subject to any disclaimer, the term of this patent is extended or adjusted under 35 U.S.C. 154(b) by 192 days.

(21) Appl. No.: 14/005,172

(22) PCT Filed: Mar. 15, 2012

(86) PCT No.: PCT/EP2012/001161
§ 371 (c)(1),
(2), (4) Date: Nov. 15, 2013

(87) PCT Pub. No.: WO2012/123122
PCT Pub. Date: Sep. 20, 2012

(65) Prior Publication Data
US 2014/0328556 A1    Nov. 6, 2014

(30) Foreign Application Priority Data
Mar. 15, 2011    (ES) .................................. 201130361

(51) Int. Cl.
*G02F 1/313* (2006.01)
*G02B 6/293* (2006.01)
(Continued)

(52) U.S. Cl.
CPC .......... *G02B 6/29376* (2013.01); *A61B 5/0066* (2013.01); *G01B 9/02028* (2013.01);
(Continued)

(58) Field of Classification Search
None
See application file for complete search history.

(56) References Cited

U.S. PATENT DOCUMENTS 5,479,546 A * 12/1995 Dumais et al. .................. 385/43
5,602,666 A *  2/1997 Ishikawa et al. .............. 398/159
(Continued)

FOREIGN PATENT DOCUMENTS

CN    1611022       4/2005
EP    0902558 A2 *  3/1999   ............ H04B 10/18
(Continued)

OTHER PUBLICATIONS

International Preliminary Report on Patentability for PCT/EP2012/001161, dated Sep. 17, 2013.*

(Continued)

*Primary Examiner* — Mike Stahl
(74) *Attorney, Agent, or Firm* — Sterne, Kessler, Goldstein & Fox P.L.L.C.

(57) ABSTRACT

A system for chromatic dispersion compensation is presented. The system includes an optical splitting element, a plurality of optical elements, and a plurality of waveguides. The optical splitting element is configured to generate at least a first beam of radiation and a second beam of radiation. The plurality of optical elements is configured to identify one or more optical paths amongst a plurality of optical paths for the first beam of radiation to travel. One of the plurality of waveguides disposed in one of the plurality of optical paths has group delay and dispersion coefficient properties per unit length that are different from group delay and dispersion coefficient properties per unit length of another one of the plurality of waveguides disposed in another one of the plurality of optical paths. The group delay and dispersion coefficient properties per unit length compensate for a chromatic dispersion associated with the second beam of radiation.

21 Claims, 8 Drawing Sheets

(51) Int. Cl.
    *G01B 9/02*    (2006.01)
    *A61B 5/00*    (2006.01)
    *G02F 1/31*    (2006.01)
    *G01N 21/47*    (2006.01)

(52) U.S. Cl.
    CPC ........ *G01B9/02058* (2013.01); *G01B 9/02091* (2013.01); *G02B 6/29394* (2013.01); *G02F 1/3137* (2013.01); *G01N 21/4795* (2013.01); *G02F 2001/311* (2013.01)

(56) References Cited

U.S. PATENT DOCUMENTS

| | | | |
|---|---|---|---|
| 5,994,690 | A | 11/1999 | Kulkarni et al. |
| 6,236,500 | B1 * | 5/2001 | Suzuki et al. ............... 359/337.5 |
| 6,546,158 | B2 * | 4/2003 | Fondeur et al. .................... 385/3 |
| 6,768,822 | B1 * | 7/2004 | Robinson et al. ............... 385/10 |
| 7,414,728 | B2 | 8/2008 | Caplan |
| 2001/0009468 | A1 * | 7/2001 | Fee ............................... 359/161 |
| 2002/0191912 | A1 | 12/2002 | Robinson et al. |
| 2003/0025917 | A1 * | 2/2003 | Suhami .......................... 356/601 |
| 2003/0053174 | A1 * | 3/2003 | Rosenfeldt .................... 359/161 |
| 2003/0099423 | A1 * | 5/2003 | Aflatooni et al. ............... 385/14 |
| 2004/0208619 | A1 * | 10/2004 | Li et al. .......................... 398/159 |
| 2005/0018201 | A1 | 1/2005 | de Boer et al. |
| 2005/0058397 | A1 | 3/2005 | Doerr |
| 2009/0076375 | A1 | 3/2009 | Maschke |
| 2010/0238452 | A1 | 9/2010 | Vanholsbeeck et al. |
| 2010/0241058 | A1 | 9/2010 | Ahmed et al. |
| 2011/0028967 | A1 | 2/2011 | Rollins et al. |
| 2012/0026462 | A1 * | 2/2012 | Uhlhorn et al. ............... 351/206 |
| 2014/0078510 | A1 * | 3/2014 | Rubio Guivernau et al. . 356/479 |

FOREIGN PATENT DOCUMENTS

| | | | |
|---|---|---|---|
| EP | 1154224 | 11/2001 | |
| WO | WO 97/37446 | 10/1997 | |
| WO | WO 01/29993 A1 * | 4/2001 | ............ H04B 10/18 |
| WO | WO 03/058858 | 7/2003 | |
| WO | WO 2005/117534 | 12/2005 | |
| WO | WO 2007/127395 | 11/2007 | |
| WO | WO 2010/011820 | 1/2010 | |
| WO | WO 2010/074321 | 7/2010 | |

OTHER PUBLICATIONS

Chinese Office Action directed to related Chinese Application No. 201280023008.9 (with English language translation), mailed Dec. 24, 2014; 17 pages.

International Search Report and Written Opinion directed to related International Application No. PCT/EP2012/001161, mailed Jun. 18, 2012; 9 pages.

Baim et al., "Utility of the Safe-Cross—Guided Radiofrequency Total Occlusion Crossing System in Chronic Coronary Total Occlusions (Results from the Guided Radio Frequency Energy Ablation of Total Occlusions Registry Study)", The American Journal of Cardiology, vol. 94, 2004; pp. 853-858.

Boppart et al., "Real-Time Optical Coherence Tomography for Minimally Invasive Imaging of Prostate Ablation", Computer Aided Surgery, vol. 6, 2001; pp. 94-103.

Guillermo Tearney et al., "High-Speed Phase- and Group-Delay Scanning with a Grating-Based Phase Control Delay Line", Opt. Lett. vol. 22, No. 23, 1997; pp. 1811-1813.

Meng Zhuo et al., "In-line measurement and compensation for dispersion in OCT system", Journal of Optoelectronics • Laser, vol. 22, No. 2, Feb. 28, 2011; pp. 256-260 (with English language abstract).

* cited by examiner

INTEGRATED SYSTEM FOR ACTIVE EQUALIZATION OF CHROMATIC DISPERSION

FIELD OF THE INVENTION

Embodiments of the invention relate to the fields of high-resolution optical coherence tomography and chromatic dispersion compensation.

BACKGROUND ART

Chromatic dispersion may result when performing optical coherence tomography (OCT) due to broadening and warping of the interference pattern, if the light is not accurately balanced between the reference and sample arm. Such dispersion causes a loss of resolution. Methods to compensate chromatic dispersion generally fall in two groups: techniques focused on the physical equalization of both arms through shaping of the corresponding dispersion relations, and techniques that rely on signal post-processing for the compensation of residual dispersion stemming from a physical imbalance. When chromatic dispersion is dependent on the scan depth, either because of the delay line, the physical configuration of the system, or the material properties of the tissue under study, physical equalization becomes more difficult. Software methods have been described for the compensation of chromatic dispersion that adapt to this situation. However, such software methods have disadvantages derived from their signal processing nature. In particular, their limited working range only allows for a moderate starting level of chromatic dispersion imbalance.

In ultrahigh resolution systems, the problem of depth-dependent chromatic dispersion is especially important, due to their low tolerance to dispersion mismatch. Additionally, systems based on integrated optics in technologies relying on strongly dispersive materials at the working wavelength (such as silicon at 1.3 µm), which try to adjust the working distance discretely by means of path-length switching schemes, also must deal with depth-dependent chromatic dispersion. Dealing with depth-dependent dispersion is also important in delay lines making use of any effect with dispersive properties, such as the thermo-optic effect in silicon at 1.3 µm.

A number of documents can be found in the patent literature regarding chromatic dispersion compensation. In particular, patent applications WO2005/117534, U.S. Pat. No. 5,994,690 and WO 2007/127395 A2 describe software-based dispersion compensation methods. In particular, application WO2005/117534 uses numerical methods for dispersion compensation; application U.S. Pat. No. 5,994,690 describes an algorithm using an autocorrelation function to correct image data, and application WO 2007/127395 A2 shows how to generate correction parameters for the compensation of dispersion.

An article by Guillermo Tearney et al. ("High-Speed Phase-and Group-Delay Scanning with a Grating-Based Phase Control Delay Line" Opt. Lett. 1997, 22 (27), pp. 1811-1813) describes a dispersion compensation system based on free-space optics and a diffraction network. However, this system can only address group velocity dispersion. The system requires discrete optics and cannot be integrated.

Patent application US2005/0058397 A1 describes a dispersion compensating system using three cascaded Mach-Zehnder interferometers to produce adjustable dispersion. Because of its interferometric working principle, its free spectral range (FSR) is limited, and there is a compromise between FSR and the maximum level of chromatic dispersion that can be obtained. The cited document describes how to use the disclosed invention to compensate dispersion in multi-channel systems by choosing a FSR, which is an integer divider of the spectral separation between channels. Based on this configuration, the compensating device is described as achromatic. Although this denomination can be appropriate for multi-channel optical communication systems, the application to OCT would require an increase in FSR of several orders of magnitude relative to telecom parameters. Additionally, this system does not allow separate adjustment of group delay, group delay dispersion, and/or higher order dispersion terms.

Another patent application publication, US 2005/0018201 A1, describes a method and apparatus to increase the detection sensitivity in OCT and for low-coherence interferometry, but it does so through spectral division of signal bands.

BRIEF SUMMARY

A system allowing physical chromatic dispersion compensation, that is suitable for integration with planar photonic circuits and that can be used in optical coherence tomography systems is provided. Additionally, such a system allows for compensation of higher order dispersion terms, and allows for arbitrary selection of group velocity, independently of the designed values of dispersion coefficients.

In an embodiment, a system for chromatic dispersion compensation is presented. The system includes an optical splitting element, a plurality of optical elements, and a plurality of waveguides. The optical splitting element is configured to generate at least a first beam of radiation and a second beam of radiation. The plurality of optical elements is configured to identify one or more optical paths amongst a plurality of optical paths for the first beam of radiation to travel. One of the plurality of waveguides disposed in one of the plurality of optical paths has group delay and dispersion coefficient properties per unit length that are different from group delay and dispersion coefficient properties per unit length of another one of the plurality of waveguides disposed in another one of the plurality of optical paths. The group delay and dispersion coefficient properties per unit length compensate for a chromatic dispersion associated with the second beam of radiation.

An example method is described. The method includes splitting a beam of radiation to form at least a first and second beam of radiation. The method further includes identifying one or more optical paths amongst a plurality of optical paths using one or more optical elements. The method further includes receiving the first beam of radiation through the identified one or more optical paths and introducing at least one of a group delay and dispersion to the first beam of radiation through the identified one or more optical paths. At least one of the group delay and dispersion introduced to the first beam of radiation through the identified one or more optical paths is different than the at least one of a group delay and dispersion introduced to the first beam of radiation through another one or more optical paths amongst the plurality of optical paths. At least one of the group delay and dispersion coefficients per unit length form a generator of the vector space of coefficients to compensate for a chromatic dispersion associated with the second beam of radiation.

BRIEF DESCRIPTION OF THE DRAWINGS/FIGURES

The accompanying drawings, which are incorporated herein and form a part of the specification, illustrate embodi- FIG. 1 illustrates a block diagram of an OCT system, according to an embodiment.

Figure 1:
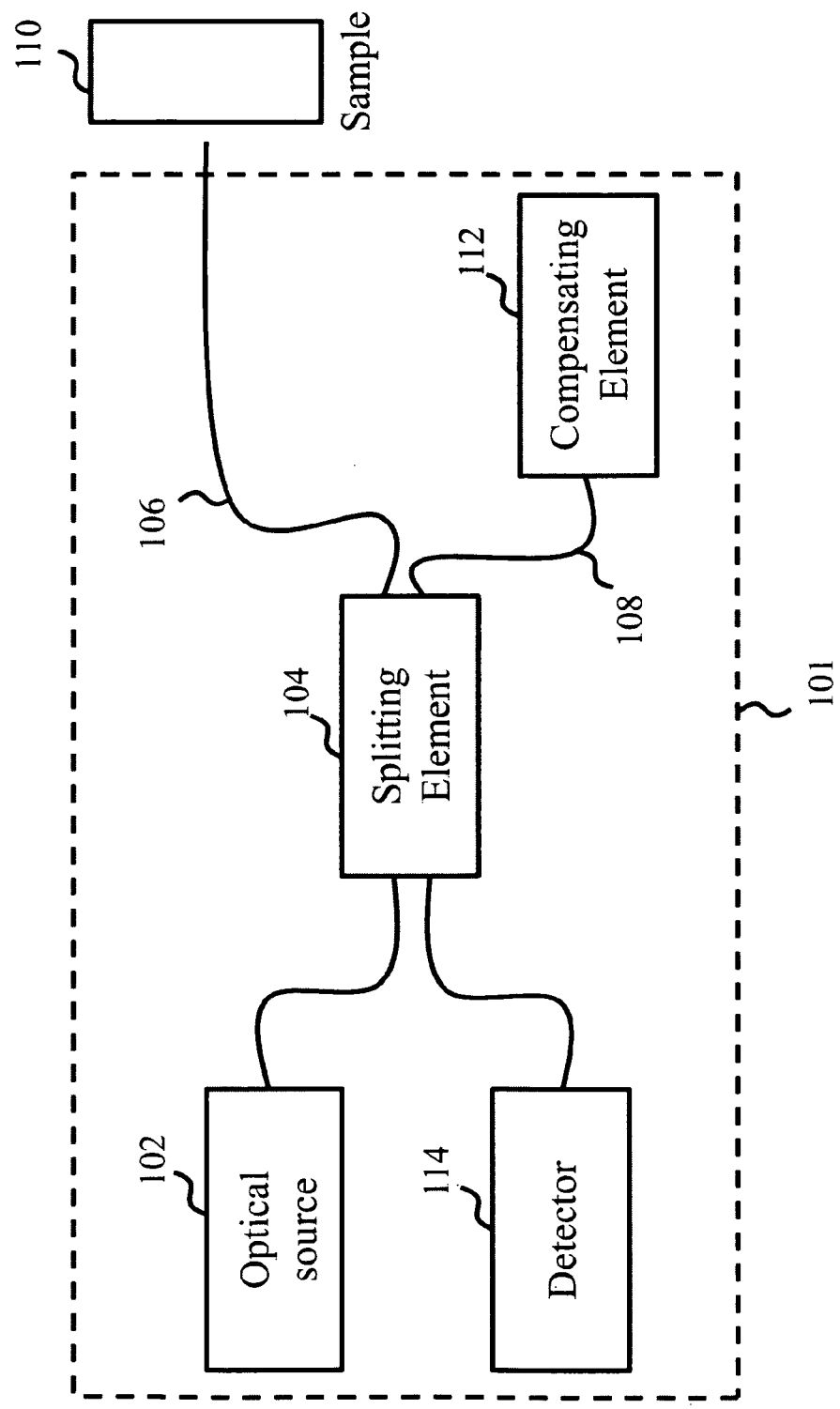

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Embodiments of the invention described herein offer a solution to the problem of chromatic dispersion in optical coherence tomography by using, for example, physical equalization that is suitable for integration through microfabrication techniques. One embodiment includes a sequential combination of waveguide segments with different dispersive properties, in such a way that the resulting chain has a desired dispersion behavior. A multiplicity of waveguide segments may be formed by chosen combinations of different waveguide lengths and types. A multiplexing configuration may be used to obtain selectable dispersion coefficients. The multiplexing can be of different types, including, for example, time-domain and frequency domain implementations. In an embodiment, the chromatic dispersion compensation system may be placed in the reference and/or sample arm of an interferometer to offer physical dispersion adjustment.

Embodiments of the invention described herein compensate for dispersion while solving the specific difficulties of integrated waveguide systems and profiting from their specific advantages. In one example, the embodied chromatic dispersion compensator is different from systems based on the introduction of macroscopic dispersive materials in free-space environments, as it does not require collimating elements, thereby producing a solution that does not interrupt the guided-wave optical path. In another example, the embodied chromatic dispersion compensator is different from numerical systems because it produces actual physical dispersion equalization between both optical arms and can be used for compensation of much larger mismatches. In another example, the embodied chromatic dispersion compensator is different from solutions based on macroscopic dispersive elements because it does not require external optical elements and may be integrated in planar optical devices. Compared to numerical systems, the embodied chromatic dispersion compensator has an advantage of a larger working range without impacting signal to noise ratio.

FIG. 1 illustrates an OCT system 101, utilizing an optical compensating element 112, and used for imaging a sample 110, according to an embodiment. For example, optical compensating element 112 may compensate for chromatic dispersion of the light within OCT system 101. The use of the term "light" may refer to any range of the electromagnetic spectrum. In an embodiment, the term "light" refers to infrared radiation at a wavelength of around 1.3 µm.

OCT system 101 further includes an optical source 102, a splitting element 104, a sample arm 106, a reference arm 108, and a detector 114. In the embodiment shown, compensating element 112 is located within reference arm 108, however, it should be understood that compensating element 112 may also be located in sample arm 106. Alternatively, compensating element 112 may be present in both sample arm 106 and reference arm 108. In one example, sample arm 106 and reference arm 108 are optical waveguides such as patterned waveguides or optical fibers. In an embodiment, all of the components of OCT system 101 are integrated onto a planar lightwave circuit (PLC). Other implementations may be considered as well, such as, for example, fiber optic systems, free-space optical systems, photonic crystal systems, etc.

It should be understood that OCT system 101 may include any number of other optical elements not shown for the sake of clarity. For example, OCT system 101 may include mirrors, lenses, gratings, splitters, micromechanical elements, etc., along the paths of sample arm 106 or reference arm 108.

Splitting element 104 is used to direct light received from optical source 102 to both sample arm 106 and reference arm 108. Splitting element 104 may be, for example, a bi-directional coupler, an optical splitter, or any other modulating optical device that converts a single beam of light into two or more beams of light.

Light that travels down sample arm 106 ultimately impinges upon sample 110. Sample 110 may be any suitable sample to be imaged such as tissue. During an OCT procedure, the light scans at a certain depth within sample 110 and the scattered radiation is collected back into sample arm 106. In another embodiment, the scattered radiation is collected back into a different waveguide than the transmitting waveguide.

Light within sample arm 106 and reference arm 108 is recombined before being received at detector 114. In the embodiment shown, the light is recombined by splitting element 104. In another embodiment, the light is recombined at a different optical coupling element than splitting element 104.

Compensating element 112 may be designed to compensate for a changing chromatic dispersion of the light within sample arm 106 that results from scanning at various depths within sample 110. Thus, in an example, compensating element 112 affects the optical properties of light in reference arm 108 to compensate for a chromatic dispersion associated with the light in sample arm 106. Various embodiments of compensating element 112 are described herein.

An active dispersion compensation system, such as compensating element 112 in one example, includes a plurality of optical paths composed of waveguide segments with different group delay and dispersion properties. This divergence in properties may result from, for example, different geometries, different core and cladding materials, periodic or quasi-periodic etching, and different doping patterns inducing dispersive properties (e.g. photonic crystals, Bragg diffraction gratings) in the light guiding region, or otherwise. Each of the waveguide segments may be characterized by a different effective refractive index. A change in the properties described above causes a change in the effective refractive index. In an embodiment, the number of segment types depends on the highest order of the chromatic dispersion to compensate for, with two types being the minimum number to adjust arbitrary combinations of group delay and second order dispersion. For example, compensating for 4th order dispersion utilizes a waveguide having four segment types. If there is a mismatch between the size and/or shape of the modes travelling in the different segments, mode spot size converters may be used to ensure adiabatic coupling between the various segments. Examples of such spot size converters include vertical and/or horizontal waveguide tapers.

In order to equalize or compensate for any combination of dispersion coefficients and group delay, vectors formed by the dispersion coefficients per unit length and the group delay per unit length of each waveguide type form a generating system of the vector space of coefficients to compensate for a given chromatic dispersion. For the final system to be compact in the general case, the vectors should exhibit sufficient linear independence.

In one embodiment, the dispersion and group delay vectors form an n-dimensional vector space, with n being the highest dispersion order for compensation. For n=2, the two waveguide types are represented by two vectors formed by the unit coefficients corresponding to group delay and second order dispersion. If these vectors are non-collinear then any point in the plane can be expressed as their linear combination. This is expressed formally in Equation 1 below:

$$\begin{pmatrix} \tau_g \\ D^2 \end{pmatrix} = \begin{pmatrix} d\tau_{g1}/dl & d\tau_{g2}/dl \\ dD_1^2/dl & dD_1^2/dl \end{pmatrix} \begin{pmatrix} l_1 \\ l_2 \end{pmatrix} \quad (1)$$

Equation 1 shows that any combination of delay ($\tau_g$) and dispersion ($D^2$) can be attained through concatenation of two waveguide segments of adequate lengths $l_1$, $l_2$. There are areas in the plane implying negative lengths for some waveguide types, but for all effects, what matters in OCT is the phase difference between the reference and sample arm. Therefore, negative lengths in one arm can be understood to be positive lengths in the opposite arm.

In an embodiment, for any chosen optical path, waveguide segments with different properties have a set of unique lengths. In one example, the lengths are calculated in such a way that all switchable paths introduce the same total group delay. In another example, the lengths are calculated in such a way that each of the paths has a different group delay (e.g. linearly spaced) but constant dispersion. In the latter example, it is possible to obtain a significant free-space scan range without suffering from waveguide related chromatic dispersion.

Figure 2:
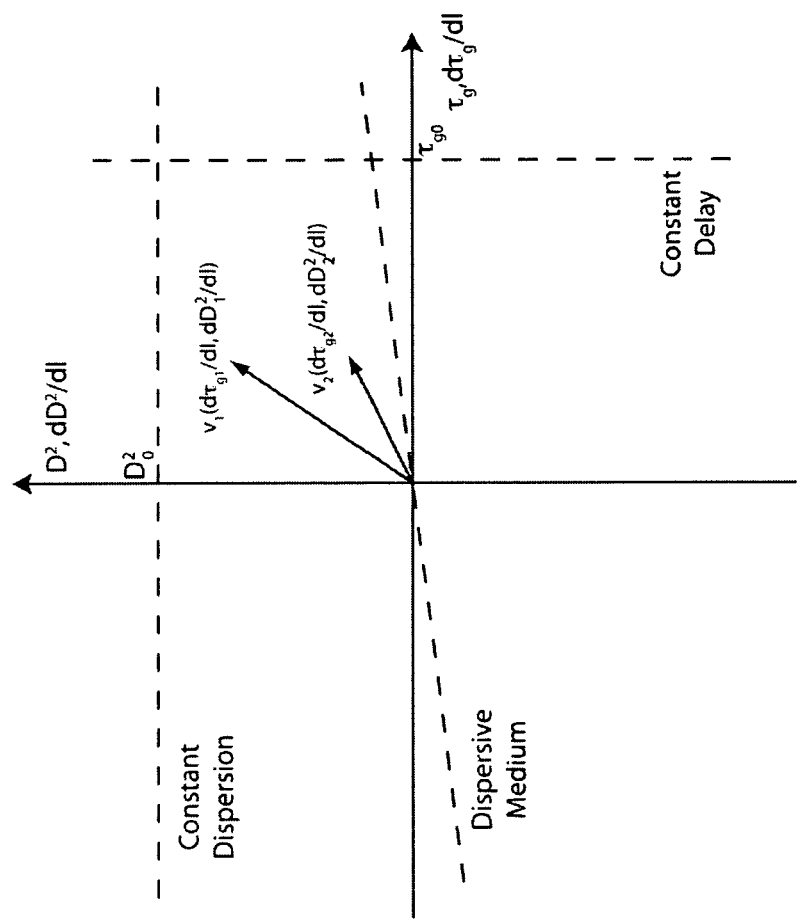
FIG. 2 illustrates a vector diagram of dispersion parameters.

FIG. 2 illustrates a vector diagram using a Cartesian coordinate system of an example case, where chromatic dispersion is compensated to second order (n=2). In the diagram, the x-axis represents group delays (and velocities) and the y-axis denotes the amount of group delay dispersion (GDD), and consequently, the group velocity dispersion (GVD). In FIG. 2, two different waveguide segments are represented by two vectors, which are formed by the two corresponding unitary coefficients.

FIG. 2 also illustrates areas defined by combinations of group delay and GDD corresponding to specific selection strategies for the effective refractive index of the waveguide segments. For example, the case where the selection of the effective refractive index of the waveguide segments leads to a constant group delay but varying GDD is illustrated as a vertical line with constant delay. In another example, the case where the selection of the effective refractive index of the waveguide segments results in each optical path inducing a different group delay and a constant GDD is illustrated as a horizontal line of constant dispersion. Also illustrated is an angled line whose slope is given by the relationship between group velocity and group velocity dispersion for a given dispersive medium, when probing various depths of the medium without dispersive effects.

Figure 3:
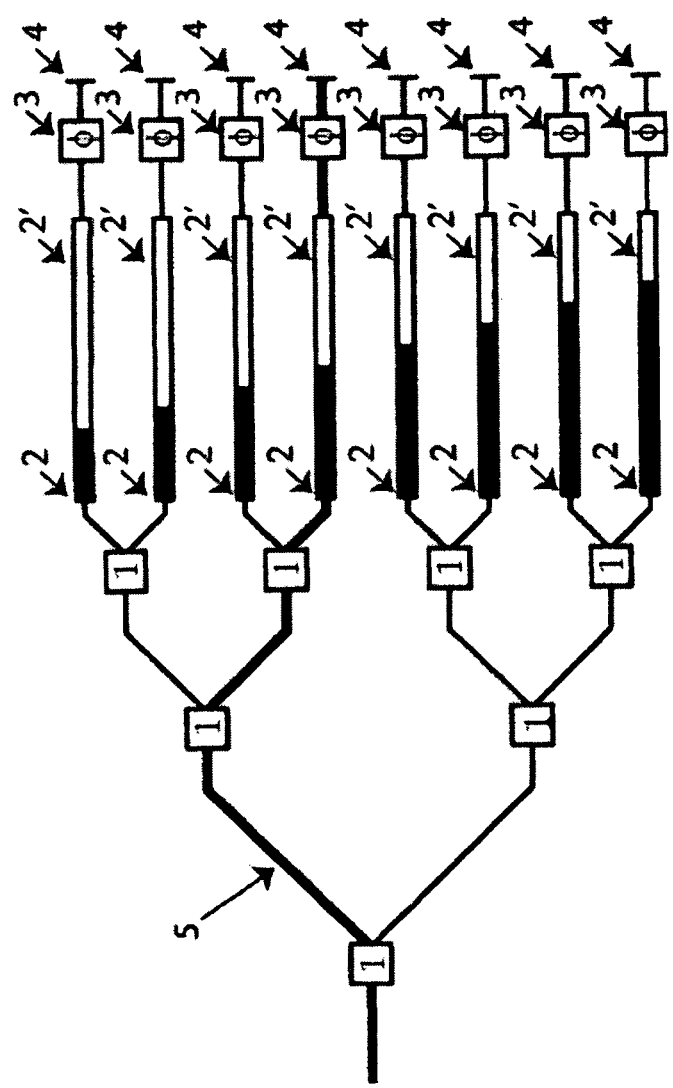
FIG. 3 illustrates a chromatic dispersion compensator, according to an embodiment.

FIG. 3 illustrates a chromatic dispersion compensator system, according to an embodiment. The system includes a plurality of switching elements 1, a plurality of waveguides each comprising two segments 2 and 2', a plurality of modulating elements 3, and a plurality of reflective elements 4.

An active optical path 5 (shown in bold) may be identified using plurality of switching elements 1. Each of switching elements 1 may be, for example, an optical switch or any modulating element that directs a majority of the incident light down one path instead of another. Each of the eight optical paths illustrated includes a waveguide having a unique combination of waveguide segments 2 and 2'. For example, each of segments 2 and 2' may be identified by a change in the waveguide width, doping profile, material, or any factor that causes a change to the effective refractive index of the particular segment.

In the case of optical coherence tomography, it is undesirable if switching elements 1 allow small but significant components of optical power to reach optical paths other than the active optical path 5. The leaked light produces a contribution to the interference pattern that appears as a perturbation source. Thus, in an embodiment, modulating elements 3 are placed in each optical path, with the purpose of applying a specific modulation (e.g. phase/frequency) to active optical path 5 and shifting the spectrum of its interference pattern as measured at a photodetector. In this way, considerable suppression of such interference sources can be obtained. Modulating element 3 may be a phase modulator and configured to suppress any interference between the various optical paths due to non-ideal light switching in switching elements 1.

In the embodiment illustrated, each optical path also includes reflective element 4. The light incident upon reflective element 4 may be returned back through the same optical path 5. Reflective element 4 may be a mirror or polished facet.

In one example, each optical path of the chromatic dispersion compensator illustrated in FIG. 3 may be chosen to compensate for a different level of chromatic dispersion present within light returning from sample 110 through sample arm 106. Various levels of chromatic dispersion may result from various scan depths within sample 110, and the resulting chromatic dispersion can be predetermined for the various scan depths. In an embodiment, plurality of reflective elements 4 are situated at the end of reference arm 108 of OCT system 101.

Although eight optical paths are illustrated, any number of optical paths may be realized along with any suitable multiplexing means for identifying amongst the paths as would be understood by one having skill in the relevant art(s) given the description herein. Furthermore, although a time-division multiplexing scheme has been illustrated using switching elements 1, it is also possible to implement a frequency-division multiplexing scheme using phase modulators to identify more than one optical path simultaneously.

Figure 4:
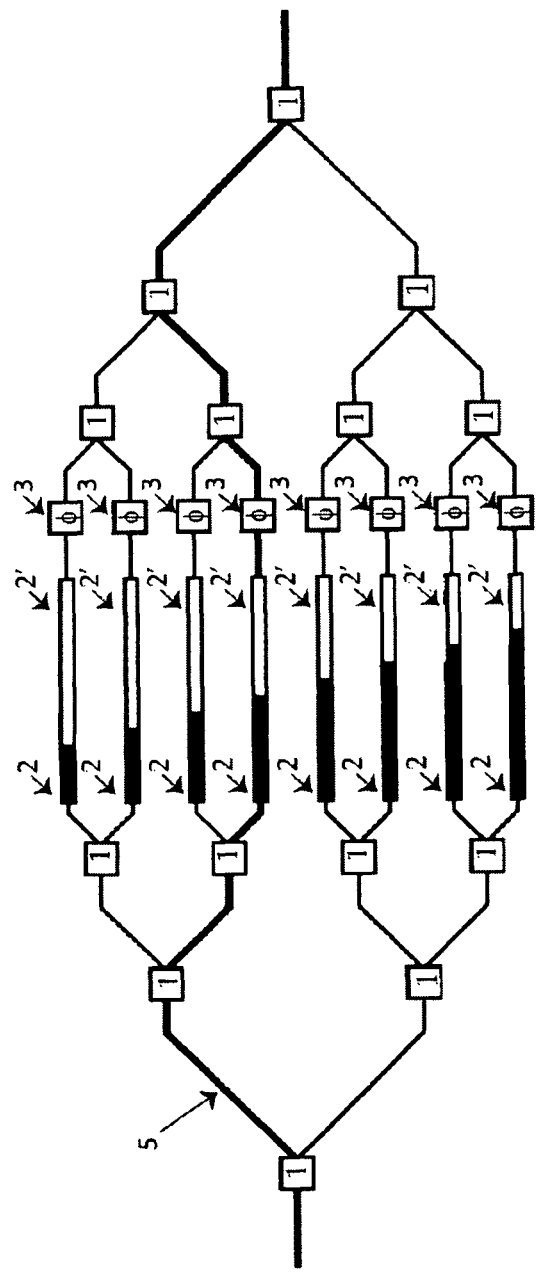
FIG. 4 illustrates another chromatic dispersion compensator, according to an embodiment.

FIG. 4 illustrates another embodiment of a chromatic dispersion compensator. Instead of including reflective elements 4, the illustrated embodiment includes a duplicate arrangement of optical paths and switching elements 1 on an opposite side of the plurality of waveguides. The duplicate arrangement may guide the dispersion-compensated light back to splitting element 104 and/or detector 114. In another example, a second network of optical paths are provided which do not mirror the arrangement of the first network of optical paths from which active optical path 5 is chosen. Such a transmission configuration as illustrated may be useful when placed within sample arm 106 of OCT system 101, according to an embodiment.

Figure 5:
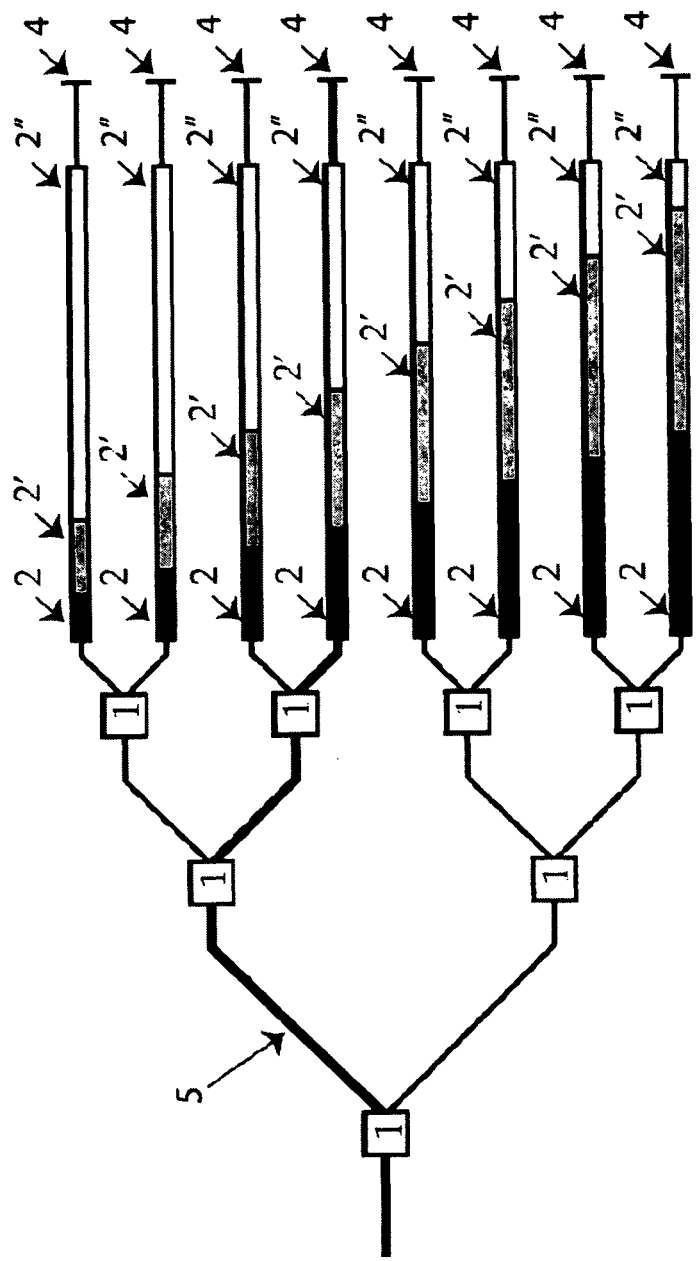
FIG. 5 illustrates another chromatic dispersion compensator, according to an embodiment.

FIG. 5 illustrates another embodiment of a chromatic dispersion compensator that does not include modulating elements 3. Additionally, each waveguide disposed along each optical path includes 3 waveguide segments 2, 2', 2", according to an embodiment. The use of three waveguide segments 2, 2', 2" allows for third order chromatic dispersion compensation (n=3).

Although previous figures illustrate switching elements 1 forming a binary tree for the identification of the desired waveguide within the plurality, it is possible to consider other architectures for path identification. In one example, optical switches may be used to inject light at different points in common waveguide segments. In another example, concatenation of various waveguide segments is done using switching elements 1.

Figure 6:
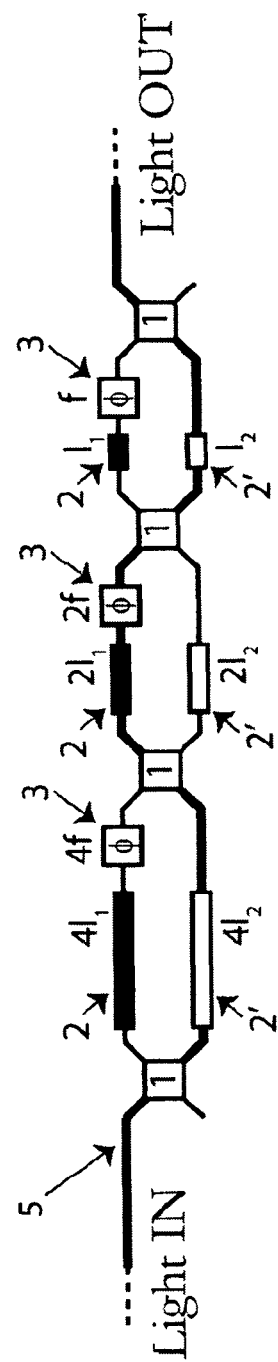
FIG. 6 illustrates another chromatic dispersion compensator, according to an embodiment.

FIG. 6 illustrates an implementation where optical path identification is done through a configuration of switching elements 1 arranged in a cascade, according to an embodiment. Switching elements 1 allow for selecting between waveguide segments 2 and 2' of different type at each stage of the cascade. Through the actuation of these switches, it is possible to direct optical power to one active optical path 5 between the 2n possible optical paths, where n is the number of stages in such a cascaded configuration. If the design of the lengths of waveguide segments 2, 2' in each alternative branch is adequate, it is possible to obtain a set of distinct points in the vector space defined by the group delay and dispersion coefficients of interest, according to an embodiment. In the embodiment shown, branch selection is binary, but switching elements 1 with more than two inputs and outputs can be considered for the compensation of higher dispersion orders.

The embodiments described above utilize waveguides with various segments identified by vectors formed by group delay and dispersion coefficients per unit length. The design and fabrication of such waveguides are described in more detail herein.

Figure 7:
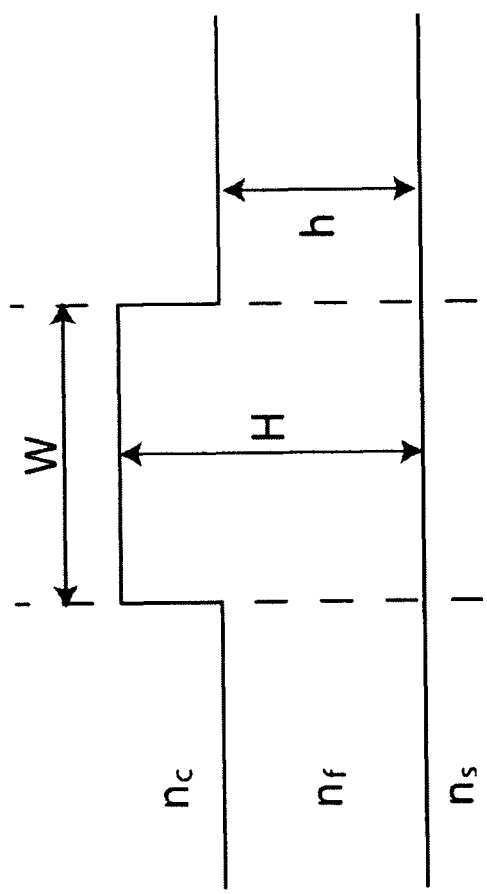
FIG. 7 illustrates a cross-section of a waveguide, according to an embodiment.

In an embodiment, rib/ridge waveguides are used because they allow for a moderately large mode size while retaining single-mode operation. The rib geometry is shown in FIG. 7, where its defining parameters are illustrated. The refractive indices of a substrate ns and a cladding nc are lower than the index of a waveguiding region nf. The relationship between a rib height H and a slab thickness h is often expressed in terms of a dimensionless parameter: $=rH$.

Conditions for single mode operation within a waveguide have been presented previously in the literature. Single mode operation may be obtained when using rectangular waveguides with a width and a height less than around 2 microns. Compared to rectangular or strip waveguides, rib/ridge waveguides allow for low-loss guiding (<1 dB/cm) as long as some effort is devoted to sidewall smoothing.

Different waveguide geometries have been studied using a program based on the Beam Propagation Method (BPM). BPM solves the Helmholtz equation under a slowly varying envelope approximation. This method is able to provide reasonably accurate solutions of the fundamental (and higher) modes in a waveguide from its cross-section. For each mode, an effective refractive index can be obtained, associated with a given propagation constant. By sweeping the excitation wavelength, the spectral behavior of, the mode is recovered. The dispersive properties of the material are not considered in the simulations, as the results contain the geometric contribution only. Indeed, intramodal dispersion is traditionally split into a component due to the waveguide behavior Dw and another component due to bulk properties of the material Dm. Although this example simulation is used herein for reference, one of skill in the art will recognize that other techniques and geometric values may instead be used.

In this example simulation, dispersion coefficients are extracted from a polynomial fit corresponding to the Taylor expansion of the propagation constant as a function of angular frequency, as shown below in Equation 2.

$$\beta(\omega) = \beta_0 + \frac{\partial \beta(\omega)}{\partial \omega}(\omega - \omega_0) + \frac{1}{2!}\frac{\partial^2 \beta(\omega)}{\partial \omega^2}(\omega - \omega_0)^2 + \frac{1}{3!}\frac{\partial^3 \beta(\omega)}{\partial \omega^3}(\omega - \omega_0)^3 + \ldots \quad (2)$$

The first three terms of the expansion (other than the constant) are the group velocity, group velocity dispersion (GVD), and the third order dispersion, respectively. In the following analysis only the first two terms are targeted for design purposes.

The simulated geometries are grouped into a first category complying with the standard single-mode condition and then into another birefringence-free category. For all geometries, a sensitivity analysis is performed with respect to the lateral dimension. Then, for a candidate waveguide technology, variations in all design parameters subject to manufacturing tolerances for waveguide dimensions H, W, h and the core refractive index have been introduced, taking into account possible temperature changes inducing thermo-optical shifts.

Different geometries are chosen for various waveguide segments. An example of chosen geometries for seven example waveguide segments are shown below in Table 1.

TABLE 1

| Geometry | W (μm) | H (μm) | h (μm) | r |
|---|---|---|---|---|
| A | 5.4 | 6.0 | 4.60 | 0.77 |
| B | 2.7 | 3.0 | 2.30 | 0.77 |
| C | 1.35 | 1.5 | 1.03 | 0.69 |
| D | 1.35 | 1.5 | 1.21 | 0.81 |
| E | 0.9 | 1.0 | 0.77 | 0.77 |
| F | 0.63 | 0.7 | 0.53 | 0.76 |
| G | 0.4 | 0.4 | 0.31 | 0.77 |

The chosen geometries cover a range of waveguide dimensions from larger dimensions as shown in segment A down to sub-micron dimensions in segment G. The obtained GVD and group delay are summarized in Table 2 below for each waveguide segment and for both the quasi-TE and quasi-TM modes.

TABLE 2

| Geometry | Quasi-TE | | Quasi-TM | |
|---|---|---|---|---|
| | $1/v_g$ [fs/cm] | GVD [fs/(cm·nm)] | $1/v_g$ [fs/cm] | GVD [fs/(cm·nm)] |
| A | 116732.86 | 0.10 | 116737.54 | 0.11 |
| B | 116930.40 | 0.37 | 116966.07 | 0.45 |
| C | 117558.69 | 1.13 | 117816.56 | 1.69 |
| D | 117401.80 | 0.94 | 117640.06 | 1.46 |
| E | 118361.64 | 1.94 | 119148.68 | 3.61 |
| F | 119422.10 | 2.64 | 121511.14 | 6.94 |
| G | 121348.09 | 2.00 | 129551.30 | 38.41 |

Table 2 shows that the waveguides are somewhat birefringent in terms of group velocity, but this effect is exaggerated with regard to dispersion when dimensions decrease. Ideally, in the embodied OCT system, dispersion compensation is performed for amounts starting at 27 fs and going up to 270 fs (corresponding to a 10 mm scan range). This requires dispersion levels in the range of 1-3 fs/(cm·nm) so that compensation can be achieved over a waveguide with a maximum total length of around 1 cm over an optical bandwith up to 100 nm, allowing for a more compact physical implementation. These geometric dispersion levels can be attained with waveguides of around 1 μm in size, but the differences between both polarization modes become too large for such shallow etch designs (factor of 2 difference or higher). Regarding manufacturing sensitivity, studies performed with respect to line width W yield reasonable stability down to waveguides with mode dimensions around 1 μm.

As discussed, changing either of the geometric dimensions H, h, W and/or refractive index of the waveguide material will change the group velocity (inverse of the group delay) and the GVD associated with the waveguide. Fabrication imperfections will have an impact on all of these variables. Table 3 below summarizes how sensitive both group velocity and GVD are to changes in these parameters for each polarization mode in a silicon waveguide having H=1.5 μm, W=0.8 μm, and r=0.39.

TABLE 3

| Polar. | Variable | S(GVD) | $S(1/v_g)$ |
|---|---|---|---|
| TE | $n_{Si}$ | -0.34 | 0.98 |
| TE | H | -1.21 | -0.03 |
| TE | h | -1.06 | -0.02 |
| TE | W | -0.07 | -0.01 |
| TM | $n_{Si}$ | -0.19 | 0.98 |
| TM | H | -1.46 | -0.03 |
| TM | h | -0.13 | -0.01 |
| TM | W | -0.54 | -0.02 |

It was found that the core refractive index is the only parameter that has a significant influence on group velocity, and the calculated sensitivity is close to 1. This is not unexpected given the strong field confinement in the core. Geometric parameters change the dispersion relation slightly, but its slope is still dominated by the material. Both polarizations exhibit the same behavior regarding the impact of perturbations on group velocity.

Overall, for this example simulation, reasonably stable behavior is observed in the dispersion coefficients. The largest sensitivity in absolute value is 1.46. Expected changes in the parameters are summarized below in Table 4, along with the estimated effect on GVD for each polarization. The assumed refractive index variation is consistent with a temperature excursion of around 80K. Vertical dimensions have been estimated from experience with common cleanroom processes. Accurate parameter tuning and the introduction of metrology and corrective process steps may further improve these values. A variation in waveguide width of 100 nm has been chosen as an acceptable fabrication tolerance.

TABLE 4

| Variable | Δx | Δx/x | Polar. | ΔGVD/GVD | $\Delta v_g/v_g$ |
|---|---|---|---|---|---|
| $n_{Si}$ | 0.02 | 0.58% | TE | -0.20% | -0.56% |
| | | | TM | -0.10% | -0.56% |
| H | 50 nm | 3.33% | TE | -4.03% | 0.09% |
| | | | TM | -4.88% | 0.10% |
| h | 50 nm | 8.55% | TE | -9.05% | 0.15% |
| | | | TM | -1.11% | 0.04% |
| W | 100 nm | 12.50% | TE | -0.88% | 0.11% |
| | | | TM | -6.78% | 0.19% |

The calculated sensitivities shown in Table 4 may be used to update the waveguide dimensions to obtain better polarization independence regarding dispersion. For example, width W may be increased by 10% to 0.88 μm while h may be decreased by 5% to 0.55 μm. These example parameters allow nearly independent modification of the properties of each polarization mode. A repetition of the previous BPM-based analysis for this new geometry leads to a GVD of 2.633 fs/(cm·nm) for the TE mode and a GVD of 2.616 fs/(cm·nm) for the TM mode.

Figure 8:
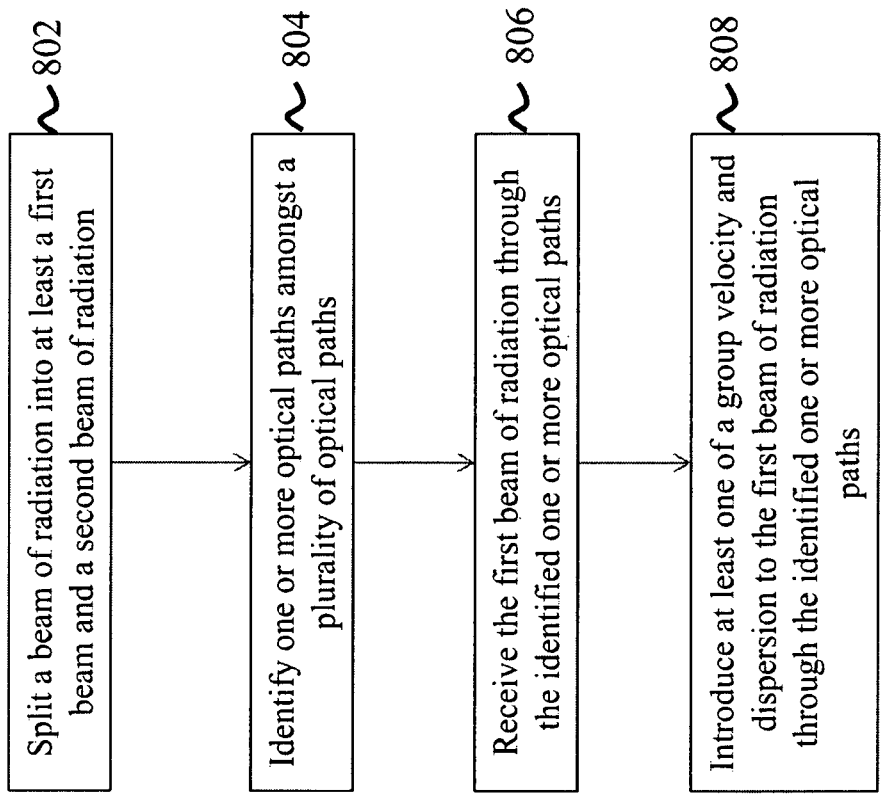
FIG. 8 is a flow chart of a method, according to an embodiment.

FIG. 8 illustrates an example method 800 for compensating for chromatic dispersion, according to an embodiment. Method 800 may be performed by various components of OCT system 101, which may include a chromatic dispersion compensator such as those illustrated in FIGS. 3-6.

At block 802, a beam of radiation is split to form at least a first and second beam of radiation. The beam of radiation may be split, for example, via an optical splitter or a bi-directional coupling device. Any or all of the beams of radiation may be confined within waveguides such as optical fibers, strip waveguides, or rib/ridge waveguides.

At block 804, one or more optical paths is identified amongst a plurality of optical paths. The identifying may be performed by an optical switch. Alternately, the identifying may be performed by optical circulators or phase modulators.

At block 806, the first beam of radiation is received through the identified one or more optical paths.

At block 808, at least one of a group delay and dispersion is introduced to the first beam of radiation through the identified one or more paths. The group delay and dispersion introduced to the first beam of radiation through the identified one or more paths is different than a group delay and dispersion that would have been introduced to the first beam of radiation through another one or more paths amongst the plurality of optical paths. Additionally, the group delay and dispersion form a generator of the vector space of coefficients to compensate for a chromatic dispersion associated with the second beam of radiation.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A system for chromatic dispersion compensation comprising:
   an optical splitting element configured to generate at least a first beam of radiation and a second beam of radiation;
   a plurality of optical elements configured to identify one or more optical paths amongst a plurality of optical paths for the first beam of radiation to travel, wherein the plurality of optical elements includes a plurality of phase modulators; and
   a plurality of waveguides, wherein one of the plurality of waveguides disposed in one of the plurality of optical paths has group delay and dispersion coefficient properties per unit length that are different from group delay and dispersion coefficient properties per unit length of another one of the plurality of waveguides disposed in another one of the plurality of optical paths, and wherein the group delay and dispersion coefficient properties per unit length compensate for a chromatic dispersion associated with the second beam of radiation.

2. The system of claim 1, wherein the group delay and dispersion coefficient properties per unit length are represented by at least two vectors.

3. The system of claim 2, wherein the at least two vectors form a generator of a vector space of coefficients to compensate for the chromatic dispersion.

4. The system of claim 1, wherein one or more of the plurality of waveguides include a plurality of concatenated waveguide segments.

5. The system of claim 4, wherein the plurality of concatenated waveguide segments are defined by a change in a geometry of at least two of the waveguide segments.

6. The system of claim 4, wherein the plurality of concatenated waveguide segments are defined by a change in material composition of at least two of the waveguide segments.

7. The system of claim 4, wherein the plurality of concatenated waveguide segments are defined by different quasi-periodic etching profiles in at least two of the waveguide segments.

8. The system of claim 1, wherein the plurality of optical elements includes a plurality of optical switches.

9. The system of claim 1, wherein the plurality of optical paths includes a plurality of branching waveguides.

10. The system of claim 1, further comprising a plurality of spot size converters coupled to the plurality of waveguides.

11. A system for chromatic dispersion compensation comprising:
    an optical splitting element configured to generate at least a first beam of radiation and a second beam of radiation;
    a plurality of optical elements configured to identify one or more optical paths amongst a plurality of optical paths for the first beam of radiation to travel; and
    a plurality of waveguides, wherein one of the plurality of waveguides disposed in one of the plurality of optical paths has group delay and dispersion coefficient properties per unit length that are different from group delay and dispersion coefficient properties per unit length of another one of the plurality of waveguides disposed in another one of the plurality of optical paths, and wherein the group delay and dispersion coefficient properties per unit length compensate for a chromatic dispersion associated with the second beam of radiation; and
    a plurality of optical modulators configured to reduce interference between the plurality of optical paths.

12. The system of claim 1, further comprising reflective elements disposed at a terminating end of at least one of the plurality of waveguides and configured to reflect the first beam of radiation to travel back through a corresponding waveguide.

13. The system of claim 1, further comprising a second plurality of optical paths on an opposite side of the plurality of waveguides.

14. The system of claim 13, further comprising a second set of optical elements configured to identify one or more optical paths amongst the second plurality of optical paths for the first beam of radiation to travel.

15. A method for chromatic dispersion compensation comprising:
    splitting a beam of radiation to form at least a first and second beam of radiation;
    identifying one or more optical paths amongst a plurality of optical paths using one or more optical elements;
    receiving the first beam of radiation through the identified one or more optical paths; and
    introducing at least one of a group delay and dispersion to the first beam of radiation through the identified one or more optical paths, wherein:
    at least one of the group delay and dispersion introduced to the first beam of radiation through the identified one or more optical paths is different than at least one of a group delay and dispersion that would be introduced to the first beam of radiation through another one or more paths amongst the plurality of optical paths, and
    at least one of the group delay and dispersion form a generator of the vector space of coefficients to compensate for a chromatic dispersion associated with the second beam of radiation.

16. The method of claim 15, wherein the identifying one or more optical paths comprises identifying using one or more optical switches.

17. The method of claim 15, wherein the identifying one or more optical paths comprises identifying one or more optical paths using one or more phase modulators.

18. The method of claim 15, wherein the introducing at least one of a group delay and dispersion comprises introducing at least one of the group delay and dispersion as vectors from an n-dimensional vector space where n is the highest dispersion order for compensation.

19. The method of claim 15, further comprising reflecting the first beam of radiation back through the identified one or more optical paths.

20. The method of claim 15, wherein the introducing at least one of a group delay and dispersion comprises passing the first beam of radiation through a waveguide comprising a plurality of concatenated waveguide segments, wherein each waveguide segment provides a different effective refractive index.

21. A system for chromatic dispersion compensation comprising:
   an optical splitting element configured to generate at least a first beam of radiation and a second beam of radiation;
   a plurality of optical elements configured to identify one or more optical paths amongst a plurality of optical paths for the first beam of radiation to travel; and
   a plurality of waveguides, wherein one of the plurality of waveguides disposed in one of the plurality of optical paths has group delay and dispersion coefficient properties per unit length that are different from group delay and dispersion coefficient properties per unit length of another one of the plurality of waveguides disposed in another one of the plurality of optical paths, and wherein the group delay and dispersion coefficient properties per unit length compensate for a chromatic dispersion associated with the second beam of radiation,
   wherein one or more of the plurality of waveguides include a plurality of concatenated waveguide segments, and wherein the plurality of concatenated waveguide segments are defined by a change in a geometry of at least two of the waveguide segments, by a change in material composition of at least two of the waveguide segments, or by different quasi-periodic etching profiles in at least two of the waveguide segments.

* * * * *